US012796716B2

(12) United States Patent
Claypool et al.

(10) Patent No.: US 12,796,716 B2
(45) Date of Patent: Nov. 17, 2026

(54) METHODS OF SELECTIVELY PROMOTING ANIMAL WELFARE THROUGH MODULATION OF MICROBIOME

(71) Applicant: DSM IP ASSETS B.V., Heerlen (NL)

(72) Inventors: Joshua Claypool, Kaiseraugst (CH); Aaron Cowieson, Kaiseraugst (CH); Kevin Freeman, Kaiseraugst (CH); Ghislain Schyns, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 485 days.

(21) Appl. No.: 18/546,238

(22) PCT Filed: Feb. 15, 2022

(86) PCT No.: PCT/EP2022/053676
§ 371 (c)(1),
(2) Date: Aug. 11, 2023

(87) PCT Pub. No.: WO2022/175265
PCT Pub. Date: Aug. 25, 2022

(65) Prior Publication Data

US 2024/0123006 A1 Apr. 18, 2024

Related U.S. Application Data

(60) Provisional application No. 63/149,808, filed on Feb. 16, 2021.

(51) Int. Cl.

| | |
|---|---|
| ***A61K 36/00*** | (2006.01) |
| ***A23K 10/30*** | (2016.01) |
| ***A23K 20/158*** | (2016.01) |
| ***A23K 20/163*** | (2016.01) |
| ***A23K 20/189*** | (2016.01) |
| ***A23K 50/75*** | (2016.01) |
| ***A61K 31/05*** | (2006.01) |
| ***A61K 31/4525*** | (2006.01) |
| ***A61K 36/06*** | (2006.01) |
| ***A61P 1/14*** | (2006.01) |

(52) U.S. Cl.
CPC ............ *A23K 20/189* (2016.05); *A23K 10/30* (2016.05); *A23K 20/158* (2016.05); *A23K 20/163* (2016.05); *A23K 50/75* (2016.05); *A61K 31/05* (2013.01); *A61K 31/4525* (2013.01); *A61K 36/06* (2013.01); *A61P 1/14* (2018.01); *C12Y 302/01092* (2013.01)

(58) Field of Classification Search
CPC .................................................... A23K 20/158
See application file for complete search history.

(56) References Cited

U.S. PATENT DOCUMENTS

2007/0036840 A1 2/2007 Tuduri et al.

FOREIGN PATENT DOCUMENTS

| | | | | |
|---|---|---|---|---|
| CN | 101331915 | | 12/2008 | |
| CN | 101331915 | A | 12/2008 | |
| CN | 103704529 | | 4/2014 | |
| CN | 103704529 | A | 4/2014 | |
| JP | 2008-019251 | A | 1/2008 | |
| WO | 2020058225 | A1 | 3/2020 | |
| WO | WO-2020097446 | A1 * | 5/2020 | ............ A61K 45/06 |

OTHER PUBLICATIONS

Xi et al, The antidepressant-like effect of trans-astaxanthin involves the serotonergic system. Oncotarget, (Apr. 11, 2017) vol. 8, No. 15, pp. 25552-25563 (Year: 2017).*
International Search Report for PCT/EP2022/053676 mailed May 31, 2022, 3 pages.
Written Opinion of the ISA for PCT/EP2022/053676 mailed May 31, 2022, 5 pages.
Wang Gen et al, "Effects of supplementing rumen-protected tryptophan on the levels of plasma tryptophan and some related metabolites in sheep", Chinese Journal of Animal Nutrition, 2018, 30(8): 3043-3054.
The First Office Action, CN Application No. 202280014657.6, May 1, 2025.
Second Review Comments Notification, CN Application No. 202280014657.6, Nov. 26, 2025.
Translation of Chinese Study on Oligosaccharides in Laying Hens, Poultry Farming and Disease Prevention, Issue 7, 2009.
Labaque, M.C., et al, "Effects of thymol feed supplementation on female Japanese quail (*Coturnix coturnix*) behavioral fear response", Animal Feed Science and Technology, 183 (2013) 67-72.

* cited by examiner

*Primary Examiner* — Qiuwen Mi
(74) *Attorney, Agent, or Firm* — NIXON & VANDERHYE P.C.

(57) ABSTRACT

The present disclosure relates to methods of feeding animals by providing feed additives that modulate the gut microbiome improve the health and welfare of the animal. The present disclosure further relates to methods of modulating level of secondary metabolites present in the gastrointestinal tract of an animal. Such modulation includes, for example, modulating the level of tryptophan metabolism derivates.

10 Claims, 1 Drawing Sheet

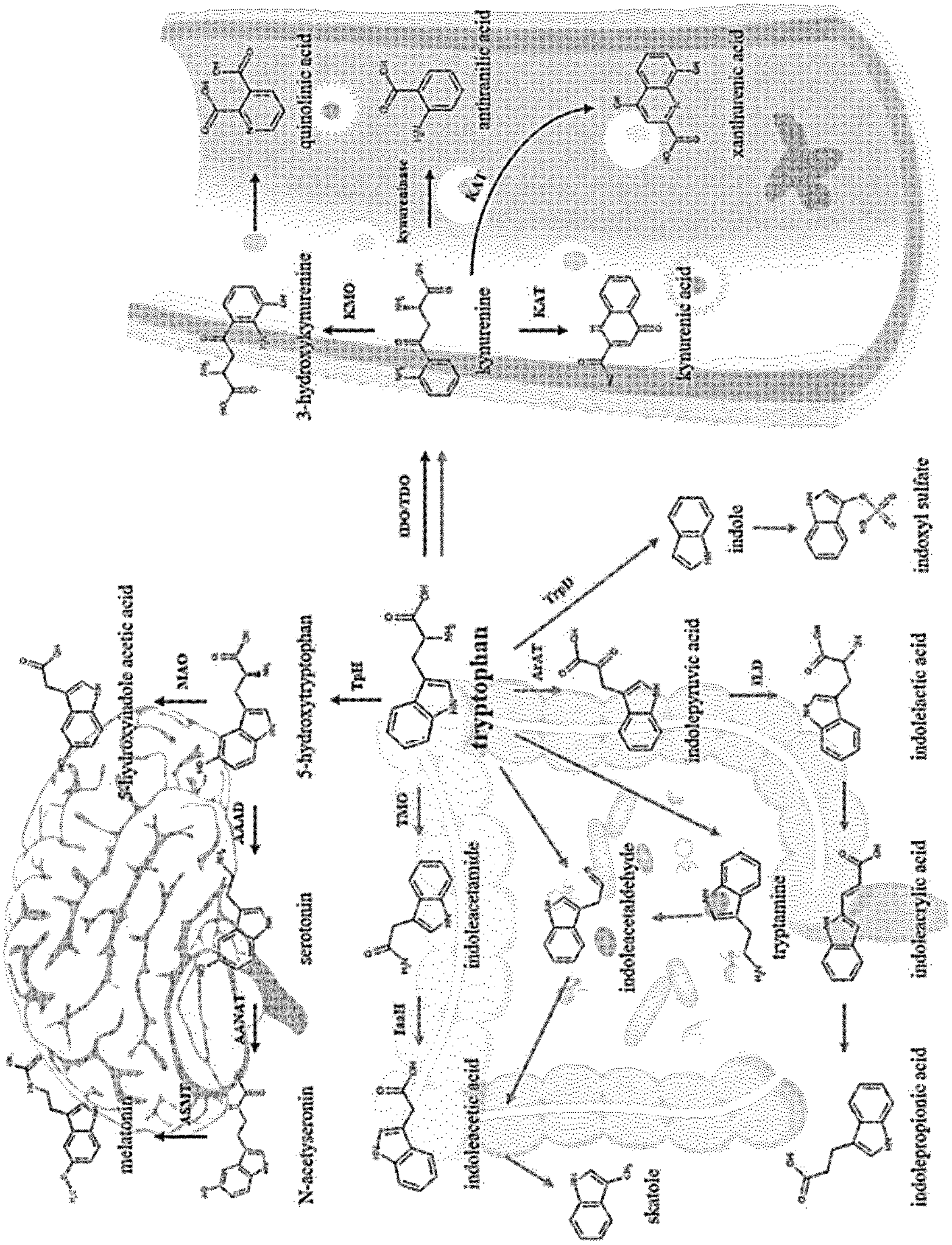
melatonin
ASMT
N-acetylserotonin
AANAT
serotonin
AAAD
5-hydroxytryptophan
TpH
5-hydroxyindole acetic acid
MAO
indoleacetic acid
IaaH
indoleacetamide
TMO
tryptophan
skatole
indoleacetaldehyde
tryptamine
indolepropionic acid
indoleacrylic acid
indolelactic acid
ILD
indolepyruvic acid
ArAT
TrpD
indole
indoxyl sulfate
IDO/TDO
kynurenine
KMO
3-hydroxykynurenine
KAT
kynurenic acid
kynureninase
anthranilic acid
quinolinic acid
KAT
xanthurenic acid

METHODS OF SELECTIVELY PROMOTING ANIMAL WELFARE THROUGH MODULATION OF MICROBIOME

CROSS-REFERENCE TO RELATED APPLICATIONS

This application is the U.S. national phase of International Application No. PCT/EP2022/053676 filed Feb. 15, 2022 which designated the U.S. and claims priority to U.S. Provisional Patent Application No. 63/149,808 filed Feb. 16, 2021, the entire contents of each of which are hereby incorporated by reference.

TECHNICAL FIELD

The present invention pertains to a method for improving the health of production animals. In particular the invention pertains to methods for improving the welfare of production animals, decreasing systemic inflammation of production animals, decreasing local inflammation of production animals, and reducing the light regimen into the daily circadian rhythm. The improvement of the health of production animals is achieved by feeding the animals with food which can regulate the tryptophan-derived metabolites in the gut or blood of the animal.

BACKGROUND INFORMATION

Raising of production animals (livestock) has been largely industrialized. Animals are raised in large flocks within a confined space. Feeding of the animals is highly adjusted to maximize the growth of meat of the animal as is light and climate control. With the help of science and modern technology, it was made possible to shorten the time period of raising production animals and at the same time maximize the meat production. However, such hastened growth does generate many problems to the animal. It has been observed that raising a large flock of animals in a confined space, if done improperly, could harm the social welfare of the animal. For example, animals such as chickens may develop social disturbance behavior such as feather pecking against their peers. In another example, chickens which have been subjected to prolonged illumination time have social disturbance behaviors. It was known that illumination is an important factor affecting the circadian rhythms of animals. Long time exposure to the light cycle can change the circadian rhythm systems of animals and thus affect the health of their reproduction, metabolism, immunity and nerve systems (Wang et al., 2002, PeerJ, DOI 10.7717/peerj.9638). Thus, there is a need for a method of improving the health of production animals which are raised in a confined space and an accelerated growth schedule. There is further a need to solve this problem by not using complicated and inorganic solutions such as medicine or genetic engineering, but a much simpler and low-cost solution.

Secondary metabolism refers to pathways and small molecule products of metabolism that are involved in ecological interactions. Unlike primary metabolism which is absolutely required for the survival of the organism, secondary metabolisms play a major role in the adaptation of organisms to their environment. Secondary metabolism occurs mainly in bacteria during the stationary phase of growth and is concomitant with a switch in energy and carbon flux away from biomass production toward the production of small, bioactive molecules (secondary metabolites) (Ruiz et al., 2010, Critical Reviews in Microbiology, Vol 36, Issue 2, pp 146-167). In the context of the production animals, the secondary metabolites produced by the microbiome residing in the digestive system of its host animal are very important for interspecies communication and behavior of both the microbiome and its host.

Traditionally, the approaches for improving the health of production animals were focusing on direct intervention with the organs of the animal by means of pharmaceuticals. Given the increasing knowledge about secondary metabolism and metabolites, there is a need to identify novel ways of enhancing the health of production animals by influencing the microbiome in the gut of the animal. In other words, there is a need to identify novel ways of influencing the production of secondary metabolites which are produced by microbiome and able to regulate the behavior of the host animal.

SUMMARY OF THE INVENTION

The present invention is directed to a method for improving the health of a group of production animals kept in a confined space, the method comprising increasing the ratio of kynurenine:tryptophan in the body of said group of animals by feeding said group of production animals one of more of the following feed additives: oligosaccharides, essential oils selected from the group consisting of thymol, eugenol and piperine, vitamin B5, vitamin B6, and tryptophan, wherein the ratio of kynurenine:tryptophan in the digestive system of said group of animals is increased for at least 10% higher than the ratio of kynurenine:tryptophan in the body of a control group of animals which are fed with the same diet except for said feed additives. In one embodiment, the ratio of kynurenine:tryptophan is measured in the feces or blood of said animals. In some embodiments, improvement of health comprises providing one of more of the following benefits to the production animals: improving the welfare of the production animals, decreasing systemic inflammation of the production animals, decreasing local inflammation of the production animals, and restoring the light regimen to the daily circadian rhythm of the production animals. Examples of improvement of welfare include reducing social disturbance and reducing feather pecking among the production animals.

The present invention is also directed to a method for improving the health of a group of production animals kept in a confined space, the method comprising increasing the ratio of peripheral serotonin:tryptophan in the digestive system of said group of animals by feeding said group of production animals one of more of the following feed additives: oligosaccharides, essential oils selected from the group consisting of thymol, eugenol and piperine, vitamin B5, vitamin B6, and tryptophan, wherein the ratio of peripheral serotonin:tryptophan in the brain of said group of animals is increased for at least 20% higher than the ratio of peripheral serotonin:tryptophan in the digestive system of a control group The present invention is further directed to a method for improving the health of a group of production animals kept in a confined space, the method comprising increasing the ratio of melatonin:tryptophan in the digestive system of said group of animals by feeding said group of production animals one of more of the following group of feed additives: oligosaccharides, essential oils selected from the group consisting of thymol, eugenol and piperine, vitamin B5, vitamin B6, and tryptophan, wherein the ratio of melatonin:tryptophan in the digestive system of said group of animals is increased for at least 10% higher than the ratio of melatonin:tryptophan in the digestive system of a control group of animals which are fed with the same diet except for said group of feed additives.

In one embodiment, the ratio of melatonin:tryptophan or serotonin:tryptophan is measured in the feces or blood of said animals. In some embodiments, improvement of health comprises providing one of more of the following benefits to the production animals: improving the welfare of the production animals, decreasing systemic inflammation of the production animals, decreasing local inflammation of the production animals, and restoring the light regimen to the daily circadian rhythm of the production animals. Examples of improvement of welfare include reducing social disturbance, reducing feather pecking among the production animals, and restoring the natural photoperiod of said group of production animals.

The present invention is also directed to a method for improving the health of a group of production animals kept in a confined space, the method comprising decreasing the ratio of tryptamine:tryptophan in the digestive system of said group of animals by feeding said group of production animals one of more of the following feed additives: oligosaccharides, essential oils selected from the group consisting of thymol, eugenol and piperine, vitamin B5, vitamin B6, and tryptophan, wherein the ratio of tryptamine:tryptophan in the digestive system of said group of animals is decreased for at least 20% lower than the ratio of tryptamine:tryptophan in the digestive system of a control group of animals which are fed with the same diet except for said feed additives.

In one embodiment, the ratio of tryptamine:tryptophan is measured in the feces or blood of said animals. In some embodiments, improvement of health comprises providing one of more of the following benefits to the production animals: improving the welfare of the production animals, decreasing systemic inflammation of the production animals, decreasing local inflammation of the production animals, and restoring the light regimen to the daily circadian rhythm of the production animals. In some embodiments, improving performance of said group of production animals comprises providing one of more of the following benefits to said group of production animals: improving nutrient absorption, reduce gut peristaltic motility, improving vitamin absorption, and improving feed enzymatic processing. Examples of improvement of welfare include reducing social disturbance and reducing feather pecking among the production animals.

BRIEF DESCRIPTION OF DRAWINGS

FIG. 1 is a diagram showing the pathways of tryptophan metabolism in animals. It is adopted from Liu et al., 2020, Trends in Endocrinology and Metabolism 31: 818-833.

DETAILED DESCRIPTION OF THE INVENTION

Definitions

A production animal (also referred to as livestock) is any animal that is kept to raise meat, fiber, protein, milk, eggs, wool, skin or other products for use by humans, as opposed to companion animals which are kept for primarily for a person's company, protection, or entertainment. The keeping of production animals includes day-to-day care, selective breeding, and the raising of animals. Typical production animals are swine, bovine, fish, sheep and poultry.

A confined space can be any closed or semi-closed area designed to restrict, and preferably prevent, the free movement of an animal to an area outside of the confined space, such as a stable, paddock, fenced land, a container, sea pen etc.

Animal welfare means how an animal is coping with the conditions in which it lives. An animal is in a good state of welfare if it is healthy, comfortable, well nourished, safe, able to express innate behavior, and if it is not suffering from unpleasant states such as pain, fear, and distress. Parameters by which animal welfare can be measured are the general impression the animal provides, the presence of wounds, its ability to freely move, the number of dead animals in the neighborhood of the animal, the presence of bite marks, the presence of feather pecking behavior etc.

Raising animals means the production of animals, regardless of the purpose. Thus, "raising animals" includes raising animals for meat and/or egg production. Chickens that are bred for meat production are broiler chickens.

Method of Improving the Health of Production Animals

In this invention, a method of improving the health of a group of production animals is shown. A preferred embodiment of the method of the invention relates to a method of improving the health of a group of production animals by modulating the amount of secondary metabolites. An also preferred embodiment of the method of the invention relates to a method of improving the health of a group of production animals by modulating the amount of one or more secondary metabolites which are produced in related metabolism pathways. In a specific embodiment, the above secondary metabolites are tryptophan derivatives. An also preferred embodiment of the method of the invention relates to a method of improving the health of a group of production animals by influencing the ratio of one of more of the following pairs of secondary metabolites: kynurenine:tryptophan, serotonin:tryptophan, melatonin:tryptophan, and tryptamine:tryptophan.

Tryptophan (Trp or Tryp) is an essential amino acid involved in the metabolic pathways for serotonin and subsequently melatonin and for nicotinamide adenine dinucleotide (NAD+). Tryptophan's fate is represented in FIG. 1. In humans, partitioning of the kynurenergic pathway and serotonergic pathway is reported to stand at 90%:10% of the tryptophan pool. Tryptophan can also produce the neuromodulator tryptamine. Tryptamine is a trace amine neuromodulator (Gao et al. 2018 Front Cell Infect Microbiol 8:13), similar to the cathecholamine neurotransmitters. Trace amines have effects both on the central nervous system (and are therefore involved in the so-called gut-brain axis), but also in the gut lumen where they act on enterocytes. As a trace amine, tryptamine is believed to act as agonist on trace amine-associated receptor TAAR1, involved into energy metabolism and immunomodulation, thereby mediating a host-nutrition-microbiota dialog (Gainetdinov et al. 2018 Pharmacol Rev 70 (3):549-620).

Surprisingly, inventors of present application have found that a few selected nutritional interventions termed eubiotics such as essential oils, vitamins B5 and B6 and tryptophan can cause an increased presence of certain secondary metabolites, such as tryptophan derivatives, in the gut and blood of the host animal. In other words, important catabolic metabolites of tryptophan, such as tryptamine, anthranilate, kynurenine, serotonin and melatonin have been seen in this invention to be either positively or negatively associated with nutritional interventions in a metabolomics study. The selected nutritional interventions, such as adding oligosaccharides, essential oils, vitamins B5 and B6, and/or tryptophan in the feed, cause the microbiome of the host animal to modulate (increase or decrease) the amounts of secondary metabolites such as tryptophan derivatives. These derivative compounds subsequently regulate the physiological and psychological functions of the host animal and thus improve the health and welfare of the host animal.

It has been observed in the present invention that the health of the host animal is improved in four aspects. First, welfare of the group of production animals is improved. It is a common problem for monogastric animals such as chicken and ducks raised in a confined space to develop social disturbance behaviors such as feather pecking or tail biting. Disturbance behaviors like this cause poor welfare of the production animal and thus has been a persisting problem for animal farmers. The method according to the invention helps to improve the welfare of animals.

Second, the health of the host animal can be improved by way of decreasing systemic inflammation of the animal. Systemic inflammation is the result of release of pro-inflammatory cytokines from immune-related cells and the chronic activation of the innate immune system. It contributes to the development of chronical disease conditions in animals. The method according to the invention helps to reduce systemic inflammation of the animal.

Third, the health of the host animal can be improved by way of decreasing local inflammation of the animal. Local inflammation occurs within the area affected by the harmful stimulus. Acute local inflammation develops within minutes or hours following a harmful stimulus, has a short duration, and primarily involves the innate immune system. The method according to the invention helps to reduce local inflammation of the animal.

Fourth, the health of the host animal can be improved by way of reducing the light regimen/duration into the daily circadian rhythm of the animal (Soliman and Hassan 2019 Veterinary World 12(7): 1052-1059). The circadian rhythms associated with light have important effects on the growth of production animals. In the production animal farming business, one way for increasing the growth rate and meat production is by prolongation of the illumination. In some extreme cases, the illumination on poultry is extended to 23 hours a day, leaving the poultry under darkness for only one hour a day. Although such a method may increase productivity, it has negative impacts on the health as well as the welfare of the animal. It has been observed that the melatonin level of chicken under the 23 hours light and 1 hour darkness period treatment was lowered to less than half of the amount of melatonin of the chicken which are under the 16 hours light and 8 hours darkness period treatment. The method according to the present invention helps to increase the amount of melatonin and its precursor serotonin and thus restore the level of melatonin in animals which are subjected to prolonged illumination. Since artificially prolonged photoperiod leads to abnormal behavior such as aggressive interactions (tail biting, feather pecking, mobility/motility issues etc.) in poultry, restoring of melatonin level in such animals helps to improve the welfare of the animals.

It has been observed in the present invention that the health benefits described above can be achieved by increasing the ratio of kynurenine:tryptophan in the body of production animals. Kynurenine is known as a neuromodulator of stress. Birkl et al. (2020, Front Vet Sci 6:209) has monitored the kynurenine/tryptophan ratio in relation to feather pecking specifically, and more generally social disturbance in laying hens. They have found that lower KYN/TRP ratio are linked to higher social disturbance profile. It is reasoned by the inventors of the present application that an increase of kynurenine/tryptophan ratio could reduce social disturbance behavior, and this produces a positive effect on the animal welfare. Surprisingly, the inventors of the present application identified a number of selected feed additives which can increase the kynurenine/tryptophan ratio in the body of production animals, and thus improve the health and welfare of the animals.

In one embodiment of the method according to the invention, the health and welfare benefits described above can be achieved by increasing the ratio of kynurenine:tryptophan in the body of production animals at least 10% higher than the ratio of kynurenine:tryptophan in the body of a control group of animals. In some embodiments, the increase of kynurenine:tryptophan ratio is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, or at least 40%. In some embodiment, the test group of animals is fed with a group of feed additives comprising one or more of oligosaccharides, essential oils selected from the group consisting of thymol, eugenol and piperine, vitamin B5, vitamin B6, and tryptophan.

It has been observed in the present invention that the health and welfare benefits described above can be achieved by increasing the ratio of peripheral serotonin:tryptophan in the body of production animals. In one embodiment of the method according to the invent, the health benefits described above can be achieved by increasing the ratio of serotonin:tryptophan in the body of production animals for at least 10% higher than the ratio of serotonin:tryptophan in the body of a control group of animals. In some embodiments, the increase of serotonin:tryptophan ratio is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, or at least 40%. In some embodiment, the test group of animals is fed with a group of feed additives comprising one or more of oligosaccharides, essential oils selected from the group consisting of thymol, eugenol and piperine, vitamin B5, vitamin B6, and tryptophan.

Serotonin within the central nervous system cannot cross the blood/brain barrier, but tryptophan can. Therefore, higher tryptophan in the gut means more tryptophan will cross the blood/brain barrier and be transformed into central serotonin. Serotonin is the precursor of melatonin. An increase in serotonin level will cause the increase in melatonin level.

It is known that melatonin and its precursor serotonin can impact the production of insulin and glucagon. An increase in the melatonin concentration can enhance the level of insulin and glucagon in animal body. It is also known that increased levels of insulin and glucagon enhance the synthesis of fat.

Both insulin and melatonin are involved in regulating circadian rhythm (Wang et al., 2020 PeerJ 8:e9638). Change in the light cycle affect the level of insulin and melatonin produced by the animal. The changed level of insulin and melatonin in the body of the animal in turn regulates the animal's physiological response to the light cycle change. Poultry production in general, and broiler rearing process is now going to long light time, as much as 23 hours a day.

This illumination regimen strongly impacts production performance such as faster fat gain but is detrimental to animal welfare. Inventors of the present application has discovered that by compensating melatonin production through feeding animal as described herein, a stronger serotonergic flux is going into more melatonin and thus a reduction of the illumination regimen and a better animal welfare can be achieved.

It has been observed in the present invention that the health and welfare benefits described above can be achieved by increasing the ratio of melatonin:tryptophan in the body of production animals. In one embodiment of the method according to the inventors, the health benefits described above can be achieved by increasing the ratio of melatonin: tryptophan in the body of production animals for at least 10% higher than the ratio of melatonin:tryptophan in the body of a control group of animals. In some embodiments, the increase of melatonin:tryptophan ratio is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, or at least 40%. In some embodiment, the test group of animals is fed with a group of feed additives comprising one or more of oligosaccharides, essential oils selected from the group consisting of thymol, eugenol and piperine, vitamin B5, vitamin B6, and tryptophan.

It has been observed in the present invention that the health and welfare benefits described above can be achieved by decreasing the ratio of tryptamine:tryptophan in the body of production animals. In one embodiment of the method according to the invent, the health benefits described above can be achieved by decreasing the ratio of tryptamine: tryptophan in the body of production animals for at least 10% lower than the ratio of tryptamine:tryptophan in the body of a control group of animals. In some embodiments, the decrease of tryptamine:tryptophan ratio is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 25%, at least 30%, or at least 40%. In some embodiment, the test group of animals is fed with a group of feed additives comprising one or more of oligosaccharides, essential oils selected from the group consisting of thymol, eugenol and piperine, vitamin B5, vitamin B6, and tryptophan.

It has been also demonstrated that tryptamine produced by a gut microbe was able to accelerate the whole gut transit (Bhattarai et al, 2018), therefore being able to influence nutrient absorption. Reduction of tryptamine is therefore favorable for increased animal performance.

It has been observed in the present invention that increase of ratios of kynurenine:tryptophan, melatonin:tryptophan, and peripheral serotonin and decrease of ratio of tryptamine: tryptophan are caused by adding a select number of feed additives to the feed of production animals.

In an embodiment, the feed additives are oligosaccharides. In the preferred embodiment, the oligosaccharides include but are not limited to glycan and yeast cell wall product. In order to produce the health benefits described in this application, a suitable amount of oligosaccharides is required depending on the type of animal and its stage of growth. However, a minimal amount of oligosaccharides is required in order to obtain the health benefits. In one embodiment, the oligosaccharides are at least 200 mg/L of the feed. In another embodiment, the oligosaccharides are at least 400 mg/L of the feed. In one embodiment, the oligosaccharides are between 200 and 2000 mg/L of the feed.

In another embodiment, the feed additives are vitamin B5 and B6. In order to produce the health benefits described in this application, a suitable amount of vitamin B5 and B6 is required depending on the type of animal and its stage of growth. However, a minimal amount of vitamin B5 and B6 is required in order to obtain the health benefits. In one embodiment, the vitamin B5 and B6 are between 1 and 20 mg/g of the feed. In another embodiment, the concentration of vitamin B6 is between 1-10 mg/g of the feed. In another embodiment, the concentration of vitamin B5 is between 10 and 20 mg/g of the feed.

In another embodiment, the feed additives are tryptophan, and preferably digestible dietary tryptophan. In order to produce the health benefits described in this application, a suitable amount of tryptophan is required depending on the type of animal and its stage of growth. However, a minimal amount of tryptophan is required in order to obtain the health benefits. In one embodiment, the tryptophan is between 0.1%-0.3% of the feed. In another embodiment, the concentration of tryptophan is between 0.1%-0.15%, 0.15%-0.20%, or 0.20%-0.25% of the feed. In another embodiment, the concentration of tryptophan is about 0.25% of the feed.

In another embodiment of the invention, the feed additives are essential oils. In a particular embodiment, the essential oils are selected from the group consisting of thymol, eugenol and piperine. In a preferred embodiment, the essential oils are an essential oil preparation comprising thymol, eugenol and/or piperine. In a particularly preferred embodiment, said essential oil preparation comprises at least two, preferably at least three essential oils selected from the group consisting of thymol, eugenol and piperine. One example of the mixture of essential oils is CRINA® which is commercially available from DSM Nutritional Products (Switzerland). In some embodiments, each of the essential oil in said essential oil preparation is provided in an amount of from 0.1 mg to 20 mg per kg feed (ppm), preferably in the range of from 1 mg to 10 mg per kg animal feed. In some embodiments, the essential oils in said essential oil preparation oil are provided independently from each other in the following ranges in animal feed: a) thymol between 1 ppm and 20 ppm, preferably between 1 ppm and 10 ppm; b) eugenol between 1 ppm and 5 ppm, for example 2 ppm; and c) piperine up to 1 ppm, preferably between 0.3 ppm and 0.5 ppm.

In some embodiments, said essential oil preparation may include other chemical compounds, for example at least one compound found in plants, and selected from the following group, as, per kg of animal feed: a) up to about 1 mg of propylidene, butylidene, phtalides, gingerol, and/or lavender oil; b) up to about 2 mg of decalactones, undecalactones, dodecalactones, ionones, irone, resorcinol, eucalyptol, menthol, peppermint oil, and/or alpha-pinene; c) up to about 3 mg of limonene, guajacol, anethol, linalool, and/or methyl dihydrojasmonate; d) up to about 4 mg of carvacrol, propionic, acetic or butyric acid, rosemary oil, clove oil, geraniol, terpineol, and/or citronellol; e) up to about 5 mg of amyl, benzyl salicylate, cinnamaldehyde, and/or vanilline, a plant polyphenol (tannin); and/or f) up to about 5 mg of a powder of turmeric or of an extract of curcuma. All these additional compounds may be used in combination with an emulsifying surfactant which may be selected advantageously from those of a rather hydrophilic nature, for example among polyglycerol esters of fatty acids such as esterified ricinoleic acid or propylene glycol esters of fatty acids, saccharo-esters or saccharo-glycerides, polyethylene glycol, lecithins etc.

In order to produce the health benefits described in this application, a suitable amount of essential oils is required depending on the type of animal and its stage of growth. In some embodiments, the essential oils is at least 200 ppm, at least 250 ppm, at least 300 ppm, at least 350 ppm, at least 400 ppm. At least 450 ppm, or at least 500 ppm of the feed, In some embodiments, the concentration of the essential oil in the feed is between 100-1000 ppm, between 100-800 ppm, between 100-600 ppm, between 200-500 ppm, between 200-400 ppm.

The essential oil compounds according to the invention are commercially available or can easily be prepared by a skilled person using processes and methods well-known in the prior art. The essential oil compounds can be used in highly purified forms in mixtures or in the form of natural available plant extracts or extract-mixtures. The term “extract” as used herein includes compositions obtained by solvent extraction (which are also known as “extracted oils”), steam distillation (which are also known as “essential oils”) or other methods known to the skilled person. Suitable extraction solvents include alcohols such as ethanol. By the expression “natural” is in this context understood a substance which consists of compounds occurring in nature and obtained from natural products or through synthesis. The natural substance may preferably contain at least one, preferably at least two of the compounds as defined above as main ingredient and additionally other essential oil compounds as for example capsaicin, tannin or carvacrol.

In some embodiments, the invention relates to a use of oligosaccharides, essential oils (in particular essential oils selected from the group consisting of thymol, eugenol and piperine), vitamin B5, vitamin B6, and/or tryptophan in a diet for feeding to a group of animals a) for improving the health of said group of production animals kept in a confined space, comprising increasing the ratio of kynurenine:tryptophan in the body of said group of animals, wherein the ratio of kynurenine:tryptophan in the digestive system of said group of animals is increased for at least 10% higher than the ratio of kynurenine:tryptophan in the body of a control group of animals which are fed with the same diet except for said feed additives; b) for improving the health of said group of production animals kept in a confined space, comprising increasing the ratio of peripheral serotonin: tryptophan in the digestive system of said group of animals, wherein the ratio of peripheral serotonin:tryptophan in the brain of said group of animals is increased for at least 20% higher than the ratio of peripheral serotonin:tryptophan in the digestive system of a control group of animals which are fed with the same diet except for said feed additives; c) for improving the health of said group of production animals kept in a confined space, comprising decreasing the ratio of tryptamine:tryptophan in the digestive system of said group of animals, wherein the ratio of tryptamine:tryptophan in the digestive system of said group of animals is decreased for at least 20% lower than the ratio of tryptamine:tryptophan in the digestive system of a control group of animals which are fed with the same diet except for said feed additives; and/or d) for improving the health of said group of production animals kept in a confined space, comprising increasing the ratio of melatonin:tryptophan in the digestive system of said group of animals, wherein the ratio of melatonin:tryptophan in the digestive system of said group of animals is increased for at least 10% higher than the ratio of melatonin:tryptophan in the digestive system of a control group of animals which are fed with the same diet except for said group of feed additives.

Type of Animal

The method of the present invention is applicable to production animals in general. In one embodiment, the method of the present invention is applicable to poultry.

The above mentioned feed additives may be provided to any suitable animal. In some embodiments, the animal is monogastric. It is generally understood that a monogastric animal has a single-chambered stomach. In other embodiments, the animal is a ruminant. It is generally understood that a ruminant has a multi-chambered stomach. In some embodiments, the animal is a ruminant in the pre-ruminant phase. Examples of such ruminants in the pre-ruminant phase include nursery calves.

In some embodiments, the animal is a poultry (e.g. chicken, turkey), seafood (e.g. shrimp), sheep, cow, cattle, buffalo, bison, pig (e.g. nursery pig, grower/finisher pig), cat, dog, rabbit, goat, guinea pig, donkey, camel, horse, pigeon, ferret, gerbil, hamster, mouse, rat, bird, or human.

In some embodiments, the animal is livestock. In some embodiments, the animal is a companion animal. In some embodiments, the animal is poultry. Examples of poultry include chicken, duck, turkey, goose, quail, or Cornish game hen. In one variation, the animal is a chicken. In some embodiments, the poultry is a layer hen, a broiler chicken, or a turkey.

In other embodiments, the animal is a mammal, including, for example, a cow, a pig, a goat, a sheep, a deer, a bison, a rabbit, an alpaca, a llama, a mule, a horse, a reindeer, a water buffalo, a yak, a guinea pig, a rat, a mouse, an alpaca, a dog, or a cat. In one variation, the animal is a cow. In another variation, the animal is a pig. In another variation, the animal is a sow.

Administration of Feed Additives

In some embodiments, administration comprises providing the feed additives described herein to an animal such that the animal may ingest the feed additives at will. In such embodiments, the animal ingests some portion of the feed additives.

The feed additives described herein may be provided to the animal on any appropriate schedule. In some embodiments, the animal is the feed additives described herein on a daily basis, on a weekly basis, on a monthly basis, on an every other day basis, for at least three days out of every week, or for at least seven days out of every month.

In some embodiments, the feed additives described herein is administered to the animal multiple times in a day. For examples, in some embodiments, the feed additives described herein is administered to the animal at least 1, 2, 3, 4, 5, 6, 7, 8, 9, or 10 times a day. In some embodiments, the nutritional composition, the feed additives described herein is administered to the animal at most 1, 2, 3, 4, 5, 6, 7, 8, 9, or 10 times a day.

In some embodiments, the feed additives described herein is administered to the animal multiple times in a day. For examples, in some embodiments, the feed additives described herein is administered to the animal at least 1, 2, 3, 4, 5, 6, 7, 8, 9, or 10 times a week. In some embodiments, the nutritional composition, the feed additives described herein is administered to the animal at most 1, 2, 3, 4, 5, 6, 7, 8, 9, or 10 times a week. In some embodiments, the feed additives described herein is administered to the animal every day, every other day, every 3 days, every 4 days, every week, every other week, or every month.

In some embodiments, the animal is the feed additives described herein during certain diet phases. For example, some animals are provided a starter diet between 0 to 14 days of age. In other embodiments, an animal is provided a grower diet between 15 to 28 days of age, between 15 to 35 days of age, or between 15 to 39 days of age. In still other embodiments, an animal is provided a finisher diet between 29 to 35 days of age, between 36 to 42 days of age, or between 40 to 46 days of age.

In certain embodiments, the feed additives described herein is provided to the animal during the starter diet phase, the grower diet phase, or the finisher diet phase, or any combinations thereof. In certain embodiments, the animal is poultry, and the poultry is provided a starter diet between 0 to 15 days of age, a grower diet between 16 to 28 days of age, and a finisher diet between 29 to 35 days of age. In other embodiments, the animal is poultry, and the poultry is provided a starter diet between 0 to 14 days of age, a grower diet between 15 to 35 days of age, and a finisher diet between 36 to 42 days of age. In still other embodiments, the animal is poultry, and the poultry is provided a starter diet between 0 to 14 days of age, a grower diet between 15 to 39 days of age, and a finisher diet between 20 to 46 days of age.

In some embodiments, the feed additives described herein is provided to the poultry during the starter diet phase, the grower diet phase, or the finisher diet phase, or any combinations thereof.

The feed additives described herein may be fed to individual animals or an animal population. For example, in one variation where the animal is poultry, the feed additives described herein may be fed to an individual poultry or a poultry population.

The feed additives described herein may be provided to an animal in any appropriate form, including, for example, in solid form, in liquid form, or a combination thereof. In certain embodiments, the feed additives described herein is a liquid, such as a syrup or a solution. In other embodiments, the feed additives described herein is a solid, such as pellets or powder. In yet other embodiments, the feed additives described herein may be fed to the animal in both liquid and solid components, such as in a mash.

The invention may be further characterized by any one of the following items:

Item 1: A method for improving the health of a group of production animals kept in a confined space, the method comprising increasing the ratio of kynurenine:tryptophan in the body of said group of animals by feeding said group of production animals one of more of the following feed additives: oligosaccharides; essential oils selected from the group consisting of thymol, eugenol and piperine; vitamin B5; vitamin B6; and tryptophan; wherein the ratio of kynurenine:tryptophan in the digestive system of said group of animals is increased for at least 10% higher than the ratio of kynurenine:tryptophan in the body of a control group of animals which are fed with the same diet except for said feed additives.

Item 2: The method of Item 1, wherein said ratio of kynurenine:tryptophan is measured in the feces or blood of said animals.

Item 3: The method of Item 2, wherein said improving the health of said group of production animals comprises providing one of more of the following benefits to said group of production animals: improving the welfare of said group of production animals, decreasing systemic inflammation of said group of production animals, decreasing local inflammation of said group of production animals, and reducing the light regimen into the daily circadian rhythm of said group of production animals.

Item 4: The method of Item 3, wherein said improvement of welfare comprises reducing social disturbance among said group of production animals.

Item 5: The method of Item 3, wherein said improvement of welfare comprises reducing feather pecking among said group of production animals.

Item 6: The method of any one of Items 1-5, wherein said oligosaccharidesare: glycans and/or yeast cell walls.

Item 7: The method of item 6, wherein the concentration of said oligosaccharides is between 200 and 2000 mg/L of the feed to be given to the group of production animals.

Item 8: The method of any one of Items 1-5, wherein the concentration of said essential oils is between 100 and 500 ppm of the feed to be given to the group of production animals.

Item 9: The method of Items 1-8, wherein said production animals are: broiler chickens, turkeys, ducks, layers, piglets, grower pigs, finisher pigs, and sows.

Item 10: A method for improving the health of a group of production animals kept in a confined space, the method comprising increasing the ratio of peripheral serotonin:tryptophan in the digestive system of said group of animals by feeding said group of production animals one of more of the following feed additives: oligosaccharides; essential oils selected from the group consisting of thymol, eugenol and piperine; vitamin B5; vitamin B6; and tryptophan; wherein the ratio of peripheral serotonin:tryptophan in the brain of said group of animals is increased for at least 20% higher than the ratio of peripheral serotonin:tryptophan in the digestive system of a control group of animals which are fed with the same diet except for said feed additives.

Item 11: The method of Item 10, wherein said ratio of peripheral serotonin:tryptophan is measured in the feces of said animals.

Item 12: The method of Item 11, wherein said improving the health of said group of production animals comprises providing one of more of the following benefits to said group of production animals: improving the welfare of said group of production animals, decreasing systemic inflammation of said group of production animals, decreasing local inflammation of said group of production animals, and reducing the light regimen into the daily circadian rhythm of said group of production animals.

Item 13: The method of Item 11, wherein said improvement of welfare comprises reducing social disturbance among said group of production animals.

Item 14: The method of Item 11, wherein said improvement of welfare comprises reducing feather pecking among said group of production animals.

Item 15: The method of Item 11, wherein said improvement of welfare comprises restoring the natural photoperiod of said group of production animals.

Item 16: The method of Item 15, wherein said natural photoperiod comprises at least 8 hours of darkness.

Item 17: The method of any one of Items 10-16, wherein said oligosaccharides are: glycans and/or yeast cell walls.

Item 18: The method of item 17, wherein the concentration of said oligosaccharides is between 200 and 2000 mg/L of the feed to be given to the group of production animals.

Item 19: The method of any one of Items 10-16, wherein the concentration of said essential oils is between 100 and 500 ppm of the feed to be given to the group of production animals.

Item 20: The method of any one of Items 10-16, wherein the concentration of vitamin B6 is at between 1 and 10 mg/g of the feed.

Item 21: The method of Item 20, wherein the concentration of vitamin B6 is about 5 mg/g of the feed.

Item 22: The method of any one of Items 10-16, wherein the concentration of vitamin B5 is between 10 and 20 mg/g of the feed.

Item 23: The method of Item 22, wherein the concentration of vitamin B5 is about 15 mg of the feed.

Item 24: The method of any one of Items 10-16, wherein the concentration of tryptophan is at between 0.1-0.3% of the feed.

Item 25: The method of Item 24, wherein the concentration of tryptophan is at between 0.2-0.25% of the feed.

Item 26: The method of Items 10-25, wherein said production animals are: broiler chickens, turkeys, ducks, layers, piglets, grower pigs, finisher pigs, and sows.

Item 27: A method for improving the health of a group of production animals kept in a confined space, the method comprising decreasing the ratio of tryptamine:tryptophan in the digestive system of said group of animals by feeding said group of production animals one of more of the following feed additives: oligosaccharides; essential oils selected from the group consisting of thymol, eugenol and piperine; vitamin B5; vitamin B6; and tryptophan; wherein the ratio of tryptamine:tryptophan in the digestive system of said group of animals is decreased for at least 20% lower than the ratio of tryptamine:tryptophan in the digestive system of a control group of animals which are fed with the same diet except for said feed additives.

Item 28: The method of Item 27, wherein said ratio of tryptamine:tryptophan is measured in the feces of said animals.

Item 29: The method of Item 28, wherein said improving the health of said group of production animals comprises providing one of more of the following benefits to said group of production animals: improving the performance of said group of production animals, improving the welfare of said group of production animals, decreasing systemic inflammation of said group of production animals, decreasing local inflammation of said group of production animals, and reducing the light regimen into the daily circadian rhythm of said group of production animals.

Item 30: The method of Item 29, wherein improving performance of said group of production animals comprises providing one of more of the following benefits to said group of production animals: improving nutrient absorption, reduce gut peristaltic motility, improving vitamin absorption, and improving feed enzymatic processing.

Item 31: The method of Item 29, wherein said improvement of welfare comprises reducing social disturbance among said group of production animals.

Item 32: The method of Item 29, wherein said improvement of welfare comprises reducing feather pecking among said group of production animals.

Item 33: The method of any one of Items 27-29, wherein said oligosaccharides are: glycans and/or yeast cell walls.

Item 34: The method of item 33, wherein the concentration of said oligosaccharides is y between 200 and 2000 mg/L of the feed to be given to the group of production animals.

Item 35: The method of any one of Items 27-29, wherein the concentration of said essential oils is between 100 and 500 ppm of the feed to be given to the group of production animals.

Item 36: The method of Items 27-36, wherein said production animals are: broiler chickens, turkeys, ducks, layers, piglets, grower pigs, finisher pigs, and sows.

Item 37: A method for improving the health of a group of production animals kept in a confined space, the method comprising increasing the ratio of melatonin:tryptophan in the digestive system of said group of animals by feeding said group of production animals one of more of the following group of feed additives: oligosaccharides; essential oils selected from the group consisting of thymol, eugenol and piperine; vitamin B5; vitamin B6; and tryptophan; wherein the ratio of melatonin:tryptophan in the digestive system of said group of animals is increased for at least 10% higher than the ratio of melatonin:tryptophan in the digestive system of a control group of animals which are fed with the same diet except for said group of feed additives.

Item 38: The method of Item 37, wherein said ratio of melatonin:tryptophan is measured in the feces or blood of said animals.

Item 39: The method of Item 38, wherein said improving the health of said group of production animals comprises providing one of more of the following benefits to said group of production animals: improving the welfare of said group of production animals, decreasing systemic inflammation of said group of production animals, decreasing local inflammation of said group of production animals, and reducing the light regimen into the daily circadian rhythm of said group of production animals.

Item 40: The method of Item 39, wherein said improvement of welfare comprises reducing social disturbance among said group of production animals.

Item 41: The method of Item 40, wherein said improvement of welfare comprises reducing feather pecking among said group of production animals.

Item 42: The method of any one of Items 37-41, wherein said oligosaccharides are: glycans and/or yeast cell walls.

Item 43: The method of item 42, wherein the concentration of said oligosaccharides is between 200 and 2000 mg/L of the feed to be given to the group of production animals.

Item 44: The method of any one of Items 37-41, wherein the concentration of said essential oils is between 100 and 500 ppm of the feed to be given to the group of production animals.

Item 45: The method of Items 37-44, wherein said production animals are: broiler chickens, turkeys, ducks, layers, piglets, grower pigs, finisher pigs, and sows.

Item 46: Use of oligosaccharides; essential oils, in particular essential oils selected from the group consisting of thymol, eugenol and piperine); vitamin B5; vitamin B6; and/or tryptophan in a diet for feeding to a group of animals for a) improving the health of said group of production animals kept in a confined space, comprising increasing the ratio of kynurenine:tryptophan in the body of said group of animals, wherein the ratio of kynurenine: tryptophan in the digestive system of said group of animals is increased for at least 10% higher than the ratio of kynurenine:tryptophan in the body of a control group of animals which are fed with the same diet except for said feed additives;

b) improving the health of said group of production animals kept in a confined space, comprising increasing the ratio of peripheral serotonin:tryptophan in the digestive system of said group of animals, wherein the ratio of peripheral serotonin:tryptophan in the brain of said group of animals is increased for at least 20% higher than the ratio of peripheral serotonin:tryptophan in the digestive system of a control group of animals which are fed with the same diet except for said feed additives;

c) improving the health of said group of production animals kept in a confined space, comprising decreasing the ratio of tryptamine:tryptophan in the digestive system of said group of animals, wherein the ratio of tryptamine:tryptophan in the digestive system of said group of animals is decreased for at least 20% lower than the ratio of tryptamine:tryptophan in the digestive system of a control group of animals which are fed with the same diet except for said feed additives; and/or d) improving the health of said group of production animals kept in a confined space, comprising increasing the ratio of melatonin:tryptophan in the digestive system of said group of animals, wherein the ratio of melatonin:tryptophan in the digestive system of said group of animals is increased for at least 10% higher than the ratio of melatonin:tryptophan in the digestive system of a control group of animals which are fed with the same diet except for said group of feed additives.

EXAMPLES

Example 1

Trial with Oligosaccharides-Enriched Diet (Yeast Cell Wall Product at 250 ppm in the Feed) and Control Diet, and Welfare Status of the Treated Chickens Control Feed is a commercial U.S. corn-soy starter poultry feed. Treated Feed is a commercial U.S. corn-soy starter poultry feed containing 250 ppm of a yeast cell wall product preparation. For the treated diet, the yeast cell wall product preparation is provided in a powder form and adding the powder to the mixer using a micro-ingredient balance prior to pelleting.

For the control diet, the same commercial U.S. corn-soy starter poultry feed is used without the addition of any yeast cell wall product.

The above industry-standard corn-soy poultry feeds are manufactured according to industry practices. In the treated diet, yeast cell wall product is supplemented to the control diet ay 200 ppm. A three-phase feeding program with the control diet and treated diet are conducted.

Ross 308 male broilers are placed randomly into floor pens constructed in a poultry house, with 40 birds per pen and a stocking density of about 1 square foot per bird. Pens are assigned randomly to treatment groups, with 3 statistical replicates per treatment and pen as the experimental unit.

On day 42, eight birds from the group fed with control diet and eight birds from the group fed with treated diet are selected. The live weight of each sampled bird is recorded. Each sampled bird is then euthanized via cervical dislocation followed by extraction of the cecal sample and blood sample using standard veterinary methods. Following dissection, cecal contents are transferred to 5 mL conical tubes, the weight of the cecal contents is recorded, and the contents are flash frozen to −80° C. Blood samples are transferred to 1 mL tubes and the contents are flash frozen to −80° C. A small ileal tissue sample is collected by resection from the intestinal wall, followed by prompt treatment with RNA-polymerase inhibitor.

Entire metabolomics procedure is performed at Metabolon, Inc. (North Carolina, USA). Samples are extracted with methanol under strong shaking to precipitate protein and dissociate small molecules bound or trapped into proteins, then centrifuged. The resulting extracts are divided into five fractions. Two fractions are analyzed by two separate reverse phase (RP)/UPLC-MS/MS methods using positive ion mode electrospray ionization (ESI). One fraction is analyzed by RP/UPLC-MS/MS using negative ion mode ESI. One is analyzed by HILIC/UPLC-MS/MS using negative ion mode ESI. One fraction is preserved as backup sample. All five samples are briefly removed of organic solvents by TurboVap.

The ratio of tryptophan metabolites against tryptophan, for example, melatonin:tryptophan, kynurenine:tryptophan, serotonin:tryptophan, and tryptamine:tryptophan, in the fecal sample is measured. It is observed that all these tryptophan metabolites:tryptophan ratios have increased in the broilers treated with yeast cell wall product when comparing to the untreated control group. This result suggests that the flux in the kynurenine pathway, the serotonin pathway and tryptamine pathway are all increased.

The numerical data of tryptophan metabolites:tryptophan ratio in the fecal sample is shown in Table 1. It was observed that metabolites:tryptophan ratio of the treated group is more than 10% higher than the untreated group.

TABLE 1

| metabolites:tryptophan ratio in fecal sample | Yeast cell wall enriched (250 ppm) diet group | Untreated control group |
|---|---|---|
| kynurenine:tryp ratio | 1.65 | 0.95 |
| peripheral serotonin:tryp ratio | 1.40 | 0.71 |
| melatonin:tryp ratio | 1.05 | 0.62 |
| tryptamine:tryp ratio | 0.21 | 0.40 |

The ratio of tryptophan metabolites against tryptophan, for example, melatonin:tryptophan, kynurenine:tryptophan, serotonin:tryptophan, and tryptamine:tryptophan, in the blood sample is measured. It is observed that all these tryptophan metabolites:tryptophan ratios have increased in the broilers treated with yeast cell wall product when comparing to the untreated control group, except tryptamine/tryp which has decreased. This result suggests that the flux in the kynurenine pathway, the serotonin pathway are all increased.

The numerical data of tryptophan metabolites:tryptophan ratio in the blood is shown in Table 2. It was observed that metabolites:tryptophan ratio of the treated group is more than 10% higher than the untreated group.

TABLE 2

| metabolites:tryptophan ratio in blood sample (umol/mmol) | Yeast cell wall enriched (250 ppm) diet group | Untreated control group |
|---|---|---|
| kynurenine:tryp ratio | 32 | 28 |
| peripheral serotonin:tryp ratio | 3.2 | 1.9 |
| melatonin:tryp ratio | 3.4 | 2.1 |

Reduction of Social Disturbance Behavior

Social behavior analysis is performed by five independent observers from study days 35 to 42. It is observed that the incidents of feather pecking per chicken per 10 minutes in the Yeast cell wall-enriched diet group is at least 10% lower than the untreated control group.

Example 2

Trial with Essential Oils Treated Diet (300 ppm) and Control Diet, and Welfare Status of the Treated Chickens Control Feed is a commercial U.S. corn-soy starter poultry feed. Treated Feed is a commercial U.S. corn-soy starter poultry feed containing 300 ppm of an essential oils preparation (commercial name CRINA, a product of DSM Nutritional Products LLC). For the treated diet, the essential oils preparation is provided in a powder form and adding the powder to the mixer using a micro-ingredient balance prior to pelleting. The essential oil preparation CRINA comprises thymol, eugenol and piperine.

For the control diet, the same commercial U.S. corn-soy starter poultry feed is used without the addition of any essential oils preparation.

The above industry-standard corn-soy poultry feeds are manufactured according to industry practices. In the treated diet, essential oils preparation is supplemented to the control diet ay 200 ppm. A three-phase feeding program with the control diet and treated diet are conducted.

Ross 308 male broilers are placed randomly into floor pens constructed in a poultry house, with 40 birds per pen and a stocking density of about 1 square foot per bird. Pens are assigned randomly to treatment groups, with 3 statistical replicates per treatment and pen as the experimental unit.

On day 42, eight birds from the group fed with control diet and eight birds from the group fed with treated diet are selected. The live weight of each sampled bird is recorded. Each sampled bird is then euthanized via cervical dislocation followed by extraction of the cecal using standard veterinary methods. Following dissection, cecal contents are transferred to 5 mL conical tubes, the weight of the cecal contents is recorded, and the contents are flash frozen to −80° C. A small ileal tissue sample is collected by resection from the intestinal wall, followed by prompt treatment with RNA-polymerase inhibitor.

Entire metabolomics procedure is performed at Metabolon, Inc. (North Carolina, USA). Samples are extracted with methanol under strong shaking to precipitate protein and dissociate small molecules bound or trapped into proteins, then centrifuged. The resulting extracts are divided into five fractions. Two fractions are analyzed by two separate reverse phase (RP)/UPLC-MS/MS methods using positive ion mode electrospray ionization (ESI). One fraction is analyzed by RP/UPLC-MS/MS using negative ion mode ESI. One is analyzed by HILIC/UPLC-MS/MS using negative ion mode ESI. One fraction is preserved as backup sample. All five samples are briefly removed of organic solvents by TurboVap.

The ratio of tryptophan metabolites against tryptophan, for example, melatonin:tryptophan, kynurenine:tryptophan, serotonin:tryptophan, and tryptamine:tryptophan, is measured. It is observed that all these tryptophan metabolites: tryptophan ratios have increased in the broilers treated with essential oils preparation when comparing to the untreated control group. This result suggests that the flux in the kynurenine pathway, the serotonin pathway and tryptamine pathway are all increased.

The numerical data of tryptophan metabolites:tryptophan ratio is shown in Table 3. It was observed that metabolites: tryptophan ratio of the treated group is more than 10% higher than the untreated group.

TABLE 3

| metabolites:tryptophan ratio in fecal sample | CRINA poultry plus (300 ppm) group | Untreated control group |
|---|---|---|
| kynurenine:tryp ratio | 1.42 | 0.85 |
| peripheral serotonin:tryp ratio | 1.12 | 0.58 |
| melatonin:tryp ratio | 1.12 | 0.51 |
| tryptamine:tryp ratio | 0.27 | 0.56 |

Reduction of Social Disturbance Behavior

Social behavior analysis is performed by five independent observers from study days 35 to 42. It is observed that the incidents of feather pecking per chicken per 10 minutes in the CRINA Poultry Plus treated group is at least 10% lower than the untreated control group.

The invention claimed is:

1. A method for improving the health of a group of production animals kept in a confined space, the method comprising:

feeding to the group of production animals feed additives comprised of yeast cell walls and essential oils selected from the group consisting of thymol, eugenol and piperine to thereby:

a) increase the ratio of kynurenine:tryptophan in the body of said group of animals; wherein the ratio of kynurenine:tryptophan in the digestive system of said group of animals is increased for at least 10% higher than the ratio of kynurenine:tryptophan in the body of a control group of animals which are fed with the same diet except for said feed additives;

b) increase the ratio of serotonin:tryptophan in the digestive system of said group of animals, wherein the ratio of serotonin:tryptophan in the brain of said group of animals is increased for at least 20% higher than the ratio of serotonin:tryptophan in the digestive system of a control group of animals which are fed with the same diet except for said feed additives;

c) decrease the ratio of tryptamine:tryptophan in the digestive system of said group of animals, wherein the ratio of tryptamine:tryptophan in the digestive system of said group of animals is decreased for at least 20% lower than the ratio of tryptamine:tryptophan in the digestive system of a control group of animals which are fed with the same diet except for said feed additives; and d) increase the ratio of melatonin:tryptophan in the digestive system of said group of animals, wherein the ratio of melatonin:tryptophan in the digestive system of said group of animals is increased for at least 10% higher than the ratio of melatonin:tryptophan in the digestive system of a control group of animals which are fed with the same diet except for said group of feed additives.

2. The method of claim 1, wherein the ratio of kynurenine: tryptophan is measured in the feces or blood of said animals; the ratio of peripheral serotonin:tryptophan is measured in the feces of said animals; the ratio of tryptamine:tryptophan is measured in the feces of said animals; and the ratio of melatonin:tryptophan is measured in the feces or blood of said animals.

3. The method of claim 2, wherein said improving the health of said group of production animals comprises providing one of more of the following benefits to said group of production animals: improving the welfare of said group of production animals, decreasing systemic inflammation of said group of production animals, decreasing local inflammation of said group of production animals, and reducing the light regimen into the daily circadian rhythm of said group of production animals.

4. The method of claim 3, wherein said improvement of welfare comprises reducing social disturbance among said group of production animals.

5. The method of claim 3, wherein said improvement of welfare comprises reducing feather pecking among said group of production animals.

6. The method of claim 3, wherein said improvement of welfare comprises restoring the natural photoperiod of said group of production animals.

7. The method of claim 6, wherein said natural photoperiod comprises at least 8 hours of darkness.

8. The method of claim 1, wherein the concentration of said yeast cell walls is between 200 and 2000 mg/L of feed to be fed to the group of production animals.

9. The method of claim 1, wherein the concentration of said essential oils is between 100 and 500 ppm of feed to be fed to the group of production animals.

10. The method of claim 1, wherein said production animals are selected from the group consisting of broiler chickens, turkeys, ducks, layers, piglets, grower pigs, finisher pigs and sows.

* * * * *